(12) United States Patent
Puetter et al.

(10) Patent No.: US 9,913,861 B2
(45) Date of Patent: Mar. 13, 2018

(54) ANTI-VIRALLY EFFECTIVE PHARMACEUTICAL COMPOSITION

(71) Applicant: MEDICE ARZNEIMITTEL PUETTER GMBH & CO. KG, Iserlohn (DE)

(72) Inventors: Sigurd Puetter, Iserlohn (DE); Richard Ammer, Iserlohn (DE); Michael Schmidbauer, Wuppertal (DE)

(73) Assignee: Medice Arzneimittel Puettere GMBH & Co. KG, Iserlohn (DE)

( * ) Notice: Subject to any disclaimer, the term of this patent is extended or adjusted under 35 U.S.C. 154(b) by 0 days.

(21) Appl. No.: 14/901,507

(22) PCT Filed: Jun. 27, 2014

(86) PCT No.: PCT/EP2014/063671
§ 371 (c)(1),
(2) Date: Dec. 28, 2015

(87) PCT Pub. No.: WO2014/207187
PCT Pub. Date: Dec. 31, 2014

(65) Prior Publication Data
US 2016/0143948 A1    May 26, 2016

(30) Foreign Application Priority Data
Jun. 28, 2013 (EP) .................... 13174235

(51) Int. Cl.
*A61K 33/28* (2006.01)
*A61K 31/439* (2006.01)
*A61K 31/46* (2006.01)
*A61K 31/55* (2006.01)

(52) U.S. Cl.
CPC ............ *A61K 33/28* (2013.01); *A61K 31/439* (2013.01); *A61K 31/46* (2013.01); *A61K 31/55* (2013.01)

(58) Field of Classification Search
CPC ........ A61K 33/28; A61K 31/55; A61K 31/46; A61K 31/439
See application file for complete search history.

(56) References Cited

U.S. PATENT DOCUMENTS

| 4,870,174 A * | 9/1989 | Paradies .............. A61K 9/0014 544/112 |
| 2002/0031509 A1* | 3/2002 | Ortenheim ............. A61K 35/58 424/94.67 |
| 2011/0105423 A1 | 5/2011 | Shaw et al. |

FOREIGN PATENT DOCUMENTS

EP          05138778          11/1992

OTHER PUBLICATIONS

Meditonsin package leaflet, Medice, updated Oct. 2013.*
Shoemaker, J., "Ointments and oleates especially in diseases of the skin", 1890, 2nd ed, F.A. Davis Publisher, p. 69.*
Ozcelik et al., "Cytotoxity, Antiviral and Antimicrobial Activities of Alkaloids, Favonoids, and Phenolic Acids," Pharmaceutical Biology, 2011; 49(4): 396-402.
Wheeler et al., "The Effect of Atropine Sulfate on the Course of Influenza Virus Infection," Science, vol. 100, No. 2606, Dec. 8, 1944, pp. 523-524.
Yamazaki et al., "Antiviral Effects of Atropine and Caffeine," J. gen. Virol., (1980) 50, 429-431.

* cited by examiner

*Primary Examiner* — Gina C Justice
(74) *Attorney, Agent, or Firm* — Occhiuti & Rohlicek LLP

(57) ABSTRACT

Described herein is a pharmaceutical composition comprising atropine or a salt thereof; aconitine; and mercury cyanide. The composition is useful in a method for treating a viral infection.

12 Claims, 1 Drawing Sheet

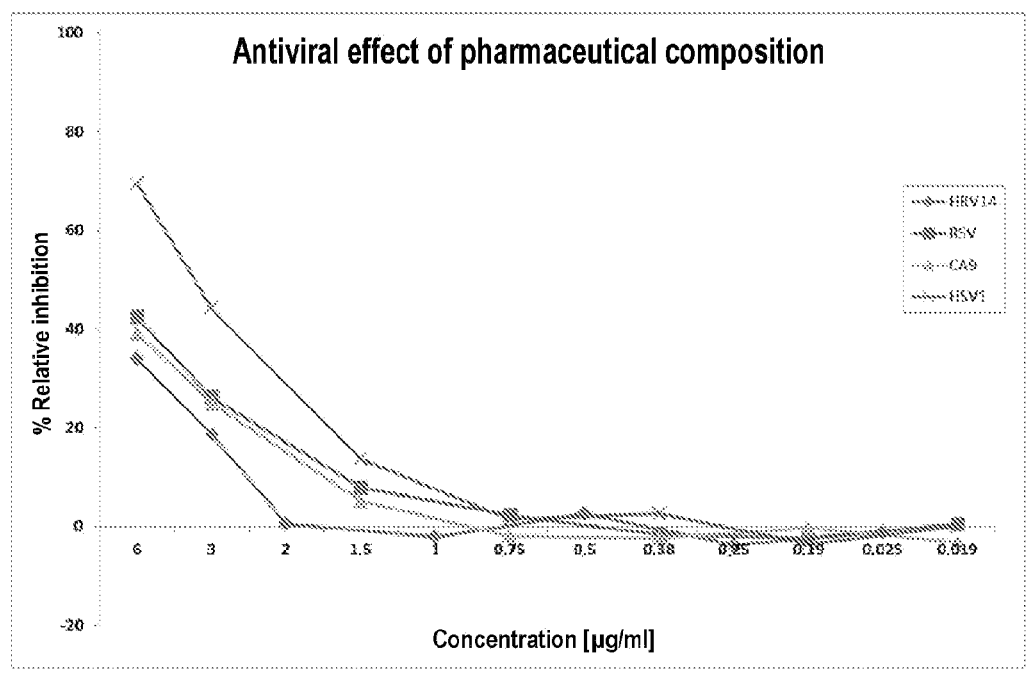

ANTI-VIRALLY EFFECTIVE PHARMACEUTICAL COMPOSITION

CROSS REFERENCE TO RELATED APPLICATIONS

This application is a U.S. National Stage Application of International Application No. PCT/EP2014/063671, filed on Jun. 27, 2014, which claims priority to European Application No. 13174235.5, filed on Jun. 28, 2013, the contents of which are hereby incorporated by reference in their entirety.

FIELD OF THE INVENTION

The present invention relates to a pharmaceutical composition comprising atropine or a salt thereof; aconitine and mercury cyanide for use in a method for treating a viral infection.

BACKGROUND OF THE INVENTION

Virues are the main pathogens of colds. Among said viruses, rhinoviruses and coronaviruses are the leaders, being responsible for 50-70% of all respiratory tract infections, followed by parainfluenza viruses, RSV, adenoviruses and enteroviruses. Influenza, another acute respiratory tract disease, is likewise caused by viruses. On top of this, herpes simplex viruses (HSV) benefit from the accompanying weakened immune system and may possibly elicit corresponding symptoms such as herpes labialis.

Whereas there is an abundance of antibiotics for treating bacterial infections, only a relatively small number of virostatics against a limited viral spectrum is available for treating virus-related diseases. Understandably, antibotics, which are associated with many adverse effects, contribute even less to curing the cold, which is usually virus related; however, they merely act against the possible bacterial secondary infections associated with a prolonged cold. The frequently premature prescription of antibiotics on a large scale is moreover associated with a high rate of resistance development or has no effect at all in a large number of cases. Therefore, effective and tolerable alternatives are desired.

Phytotherapeutics and complex homeopathics may be such an alternative. In fact, such alternatives have been and are being consistently discussed, since, with respect to the synthetic remedies, they have advantages in the form of a larger therapeutic spectrum, a better tolerability and fewer drug interactions and are not subject to the risk of resistance development.

In recent years, studies in which it was possible to demonstrate an antiviral effect of plant-based medicaments have been increasingly published. The complex homeopathic Meditonsin® consists of the plant components atropine and aconitine and the salt mercury cyanide (Mercurius cyanatus) and has already been used for over 60 years for treating inflammations of the throat, nasal cavity and pharyngeal cavity. Clinical investigations confirm the efficacy in the treatment of inflammations of the upper airways and the good tolerability.

EP 0 513 878 discloses a solution containing, inter alia, 0.10 g of cetylpyridinium chloride, 0.004 g of atropine hydrochloride and 0.004 g of mercury(II) cyanide (based on 100 ml). An antiviral efficacy of the solution against influenza viruses is described, more precisely by mercury(II) cyanide and cetylpyridinium chloride.

Wheeler et al., "The Effect of Atropine Sulfate on the Course of Influenza Virus Infection", Science, Aug. 12, 1944, Vol. 100, No. 2606, relates to the antiviral effect of atropine sulphate (influenza A viruses). However, the atropine concentration actually used is not specified. Moreover, there is no evidence of a continuous efficacy of atropine against influenza A viruses. On the contrary, the effect depends on the time of intraperitoneal administration in relation to the time of virus inoculation of the test animals.

Z. Yamazaki et al., "Antiviral Effects of Atropine and Caffeine", J. Gen. Virol. (1980), 50, 429-431, discloses the antiviral effect of atropine against herpesviruses and influenza viruses. The maximum effect is achieved at an atropine concentration of 2 mM.

Özçelik et al., "Cytotoxicity, antiviral and antimicrobial activities of alkaloids, flavonoids, and phenolic acids", Pharmaceutical Biology, 2011; 49(4): 396-402, describes, inter alia, the antiviral, antibacterial, antimycotic effect of numerous alkaloids and their cytotoxicity. An antiviral effect of atropine within the concentration range of 0.8-0.05 µg/ml, for example against HSV1, is described.

The studies underlying the present invention have revealed that, surprisingly, a mixture of atropine, aconitine and mercury cyanide has strongly antiviral properties. Particular attention was paid to the question of whether, in which concentrations and against which viruses the mixture has an effect. This involved testing against cold viruses and herpesviruses.

The present patent application therefore relates to the surprising insight that a pharmaceutical composition comprising atropine or a salt thereof, aconitine and mercury cyanide can be used in an advantageous manner for treating viral infections.

SUMMARY OF THE INVENTION

The present invention shows the antiviral properties of a mixture of the active ingredients atropine, aconitine and mercury cyanide in various concentration ranges. It was possible to demonstrate that the activity of all the viruses tested was strongly inhibited to very strongly inhibited by the mixture.

The present invention therefore relates to a pharmaceutical composition comprising atropine or a salt thereof, aconitine and mercury cyanide for use in a method for treating a viral infection.

BRIEF DESCRIPTION OF THE FIGURES

FIG. 1 reports the antiviral effect of the pharmaceutical composition according to the invention depending on the concentration, measured as percentage relative inhibition. The corresponding individual values can be found in Table 3.

DETAILED DESCRIPTION OF THE INVENTION

The present invention relates to a pharmaceutical composition comprising or substantially consisting of a) atropine or a salt thereof; b) aconitine; and c) mercury cyanide for use in a method for treating a viral infection.

The term "pharmaceutical composition", as used here, encompasses in particular peroral dosage forms, for example solid, semi-liquid or liquid compositions for oral administration. An aqueous/ethanolic solution for dropwise administration has been found here to be especially advantageous.

For example, mixtures of 94% (g/g) ethanol, 85% glycerol and purified water in the weight ratio 5:10:85 are used especially advantageously.

However, other dosage forms are also alternatively possible, for example solid peroral dosage forms such as powders, tablets or capsules. In particular, manufacturing is achieved in accordance with the standards for the manufacture of homeopathic medicaments as per Homoopathisches Arzneibuch 2012 (HAB 2012) [Homeopathic pharmacopoeia], official edition. For example, in accordance with the directions of the HAB, it is possible to manufacture triturations, in which the starting materials are rubbed to a powder with lactose monohydrate in a stepwise manner. Alternatively, it is possible to press tablets from the corresponding triturations. In this connection, limited additives of magnesium stearate or calcium behenate as lubricant and of starch as disintegrant can be used. In the case of granulation, aqueous lactose solution, ethanol and suitable concentrations of starch pastes can be used.

Moreover, it is possible to manufacture globules in accordance with HAB direction 10, wherein sugar globules are evenly wetted with 1/100 mass fractions of the relevant dilution and air-dried.

In addition to peroral dosage forms, the pharmaceutical composition of the present invention can encompass parenterals, i.e. liquid dilutions for injection, and liquid liniments, and ointments, suppositories, eye drops, nose drops which have been manufactured in accordance with HAB directions 11-15 and 45. As explained above, the present pharmaceutical composition in the most preferred embodiment is a peroral solution which has been manufactured in accordance with the directions of the Homöopathisches Arzneibuch.

The wording "substantially consists of" means that the pharmaceutical composition contains these constituents as active constituents. However, it can additionally contain one or more solvents, excipients, etc., which while being required for the manufacture of a pharmaceutical composition, do not contribute or do not substantially contribute to the pharmacological efficacy.

One of the constituents of the pharmaceutical composition is atropine. Atropine is a tropane alkaloid which is a racemate of the isomers (R)- and (S)-hyoscyamine according to the following structural formula. The (R)-form is shown at the top, the (S)-form at the bottom:

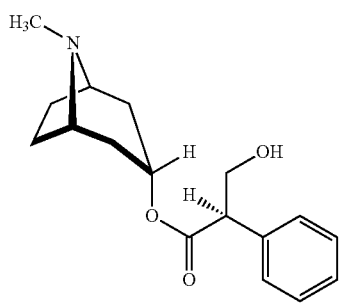

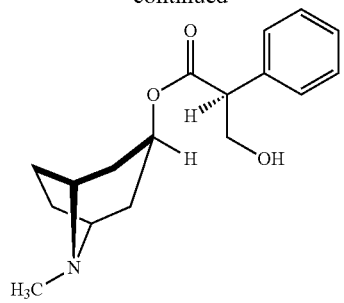

Atropine is part of the parasympatholytics and competes with the neurotransmitter acetylcholine at the muscarinic receptors of the parasympathetic nervous system. The physical effects of ingestion of atropine are as follows: speeding-up of the heart rate, dilation of the bronchi, reduced saliva formation, and much else. Furthermore, other, though infrequent, areas of use have been described, for example use in cramps of the gastrointestinal tract, in difficult urination and urinary incontinence. However, use as antiviral agent has hitherto not been described.

The atropine salt used according to the invention is usually atropine sulphate, for example atropine sulphate monohydrate.

In the composition according to the invention, atropine or its salt is used in a concentration between 1 to 100 µg/ml, preferably 1 to 10 µg/ml, more preferably 2 to 7 µg/ml and most preferably 3.13 to 6.25 µg/ml.

According to the invention, it has been found that, if atropine sulphate is used in combination with the other constituents of the pharmaceutical composition, a lower dose of atropine sulphate can be assumed (see below). In other words, at a lower concentration, it is possible to achieve an at least comparable, possibly even distinctly better, antiviral effect.

Aconitine is used as another constituent of the pharmaceutical composition. Aconitine is a diterpenoid alkaloid which slows the inactivation of the voltage-dependent sodium channel and thereby prolongs the influx of sodium ions during the action potential of the nerves. It acts in this respect firstly centrally and peripherally on motor and sensory nerves, firstly in a stimulatory manner followed by paralysis. Cardiac impacts may involve arrhythmias, bradycardia and diastolic cardiac arrest. In the case of adults, the lethal dose of aconitine is approximately 5 mg. Aconitine has the following structural formula:

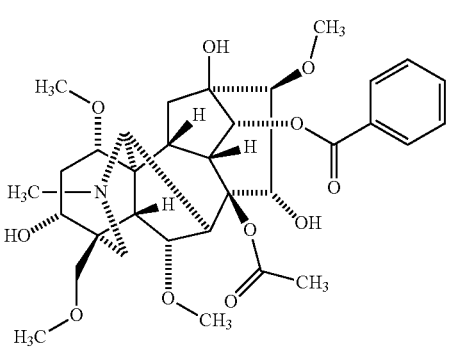

The chemical molecular formula is $C_{34}H_{47}NO_{11}$. An antiviral efficacy of aconitine has hitherto not been described.

Aconitine is used as active constituent of the composition according to the invention in a concentration between 0.05-100 μg/ml, for example 0.5-100 μg/ml, preferably 0.05-5 μg/ml, more preferably 0.5-2 μg/ml and most preferably 0.16-1.56 μg/ml aconitine. Here too, it has been found that, in combination with the other two active constituents of the pharmaceutical composition according to the invention, viz. mercury(II) cyanide and atropine, a synergistic effect can be achieved, i.e. a supra-additive antiviral effect at the same or lower dose of the individual components.

The third constituent of the pharmaceutical composition according to the invention is mercury cyanide ($Hg(CN)_2$). Mercury cyanide is a highly toxic compound which is only used in homeopathy for treating diphtheria, severe angina and colds.

Mercury cyanide is used as component of the composition according to the invention in concentrations between 0.001 to 10 μg/ml, preferably 0.001 to 0.1 μg/ml, more preferably 0.001 to 0.01 μg/ml, most preferably 0.003-0.006 μg/ml mercury cyanide in solution.

As addressed above, the pharmaceutical composition of the present invention comprises a combination of atropine (or a salt thereof), more particularly atropine sulphate, and aconitine and mercury cyanide. For such a composition, it has been found to be advantageous to prepare the concentration of each individual constituent at a lower level than in the case of the particular individual substance. For instance, the pharmaceutical composition according to the invention, for example in the form of an aqueous/ethanolic solution, can contain about 1-10 μg/ml, preferably 5 μg/ml, atropine sulphate, about 0.5-5 μg/ml, preferably 1 μg/ml, aconitine, and about 0.001-0.1 μg/ml, preferably 0.004 μg/ml, mercury cyanide.

An advantageous composition according to the present invention comprises a total concentration of approximately 3-9 μg/ml of the aforementioned ingredients. As is evident from FIG. 1, the best results with regard to antiviral efficacy are demonstrated at a total concentration of 6 μg/ml; however, even with lower values, for example a total concentration of 3 μg/ml, excellent inhibitory values were still achieved.

An especially preferred composition comprises a solution of ethanol, glycerol and water which contains about 5 μg/ml atropine sulphate, 1 μg/ml aconitine and 0.004 μg/ml mercury cyanide. As described in the introduction, such a composition is already known and has been successfully sold on the European market for decades under the name Meditonsin®. It has been found that, astonishingly, the use of the triple combination displays a synergistic effect with respect to the antiviral activity of the individual components. As can be gathered from the examples, the so-called "Meditonsin" mixture has a strong to very strong antiviral effect particularly against RSV, CA9, HRV14 and HSV1. This is the case especially when taking into account the fact that the concentrations of the individual components, as used in the mixture, are lower than the amounts used in each case for the individual tests.

Table 2 shows a comparison of the antiviral effect between the substances atropine sulphate, aconitine and mercury cyanide and also the mixture thereof. The measurement result reported is the percentage plaque inhibition. For example, the percentage plaque inhibition for the mixture of 5 μg/ml atropine sulphate, 1 μg/ml aconitine and 0.004 μg/ml mercury cyanide is, based on HSV1, 69.53%. This is a surprisingly high value when the plaque inhibition of the individual substances is taken into account: this is approximately 35% in the case of atropine sulphate, approximately 8% for aconitine and even a slightly negative value for mercury cyanide. Compared with the value to be expected from the individual measurements, the inhibitory effect of the mixture on HSV1 is almost twice as high. Apart from that, a plaque inhibition of almost 70% is an excellent value, which illustrates the high therapeutic potential of the mixture used.

Similarly astonishing results can be gathered from Table 2 with respect to CA9, RSV and HRV14. Here too, a supra-additive effect of the individual components in the mixture is revealed, which effect can be estimated to be about two-fold with respect to the individual substances.

The pharmaceutical composition of the present invention (mixture) is administered to the adult patient in a daily total dose of about 20 μg atropine sulphate, 4 μg aconitine and 0.016 μg mercury cyanide. In this connection, deviations of approximately ±30% from the specified amount are tolerable.

In other words, approximately 2-6 ml of the pharmaceutical composition are administered per day to an adult patient, with the composition having the above-specified concentrations. The dose is halved for children between the ages of 6 and 12 years, is reduced yet further for small children from the age of 1 year, and is about 25% for infants from the age of 7 months.

The present invention will now be elucidated with reference to the following exemplary embodiments, in which the effects of the composition according to the invention will be presented.

EXAMPLES

Purpose/Goal

The goal of the antiviral testing described hereinbelow was to investigate the antiviral effect of atropine sulphate, aconitine and mercury cyanide and of a mixture of these three substances.

Testing Strategy

The antiviral testing of atropine sulphate, aconitine and mercury cyanide and of a mixture of these three substances is divided into two phases. In the first phase, the cytotoxicity of the test substances is tested in various dilution levels in order to find out from which dilution level no cytotoxic effect is exerted by the test substances on the non-virus-infected cell lines serving as virus carrier. In the second phase, the antiviral effect of the test substances is investigated in various dilution levels on the viruses used in the test, starting with the test substance dilution from which no cytotoxic effect is exerted on the cell lines.

Materials

Test Samples

From the raw materials atropine sulphate (AT), aconitine (AC) and mercury cyanide (QC), the test samples for the toxicity testing and the subsequent testing for antiviral effect were prepared according to the following table.

| Consecutive number | Test substance | Amount weighed/ solubility in ethanol | Concentration | Toxicity testing, first dilution: 1:10 = highest concentration in test |
|---|---|---|---|---|
| No. 1 | Atropine sulphate (AT) | 100 mg/10 ml/ 80% ethanol | 10 mg/ml/ 80% ethanol | 1 mg/ml/ 8% ethanol |

-continued

| Consecutive number | Test substance | Amount weighed/ solubility in ethanol | Concentration | Toxicity testing, first dilution: 1:10 = highest concentration in test |
|---|---|---|---|---|
| No. 2 | Aconitine (AC) | 100 mg/10 ml/ 80% ethanol | 10 mg/ml/ 80% ethanol | 1 mg/ml/ 8% ethanol |
| No. 3 | Mercury cyanide (QC) | 10 mg/ml/ 43% ethanol | 10 mg/ml/ 43% ethanol | 1 mg/ml/ 4.3% ethanol |
| No. 4 | Mixture of Nos. 1-3 | AT: 0.05 mg in 5 ml/0.008% ethanol<br>AC: 0.01 mg in 1 ml/0.008% ethanol<br>QC: 0.00004 mg in 4 ml/ 0.000043% ethanol | | 6.004 μg/ml/ 0.004% ethanol |

Cells

Human epithelial cells (HEp-2 cells) for infections with RSV and HSV1

Buffalo Green Monkey cells (BGM cells) for infections with CA9

HeLa cells for infections with HRV14 (the HeLa cell line originates from human epithelial cells Viruses Human respiratory syncytial virus, Long strain (RSV)
Human coxsackievirus type 9 (CA9)
Human herpesvirus type 1 (HSV1)
Human rhinovirus type 14 (HRV14, major group)

Reference Controls and Laboratory Internal Standards

Ribavirin (Virazole®), ICN Pharmaceuticals, against RSV (5 μg/ml)

Laboratory internal standards (L-Std) against infections with CA9 (L-Std, 6 μg/ml)

Aciclovir (2.5 μg/ml) against HSV1

Oxymetazoline hydrochloride (OMZ, 10 μg/ml) against HRV14

Cytotoxicity Assay to Eliminate a Possible Intoxication of Cell Cultures

The cytotoxicity of the test samples was investigated by means of the MTT assay (testing of metabolism). The assay preparations for the testing of metabolic performance in the MTT assay were performed in 96-well microtitre plates, and the same assay preparations for the microscopic analyses were in 24-well microtitre plates.

MTT Assay

Principle

The determination of metabolic performance in the MTT assay was achieved by means of the quantitative analysis of mitochondrial enzymatic activity. The Mosmann colorimetric assay (Mosmann 1983) involves the conversion of the colourless MTT salt (dimethylthiazole diphenylterazolium bromide) to blue, water-insoluble formazan crystals by mitochondrial dehydrogenases. In this connection, it is possible to measure a direct correlation between the viability or metabolic performance of the cells and the enzymatic activity of the cells.

Test Protocol

The toxicity testing was carried out after the test samples were dissolved and prepared according to section 0. This was followed by further log 2 or log 10 dilution graduations for all test solutions. All test substance dilutions were added in parallel samples to growing BGM, HEp-2 and HeLa cells. Thereafter, the treated cell cultures were incubated for altogether 3 days or 5 days at 37° C. and 5% $CO_2$. The controls included were cells containing medium alone (untreated control) or containing 8, 4, 2, 1 and 0.004% ethanol in medium (ethanol control).

Evaluation

The analysis in the MTT assay was done on day 1 and day 3 or on day 1 and day 5 after addition of substance. To this end, the treated cells were incubated for another to 4 hours with the MTT solution and, after solubilization of the formazan crystals in dimethyl sulphoxide (DMSO), the optical density (OD) of the cell culture supernatants was determined in a photometer at 570 nm (RF690 nm). In the evaluation, the more cells that are damaged, the fewer formazan crystals that have formed and the lower the OD. The microscopic assessment of an altered cell morphology was done on day 3 or day 5 after addition of substance by means of the criterion of an unaltered cell morphology or by means of enlarged cells with vacuolization through to a detached cell lawn.

Calculation of Percentage Relative Viability (Excel 2000 Statistics)

The OD values of the untreated controls were defined as 100% viability. The OD values of the assay preparations were accordingly reported as percentage values (% toxicity). It was possible here, by means of multiple parallel samples, to determine the 50% inhibitory dose ($IC_{50}$) in dose-response curves of the various test samples through to the concentration exhibiting no test substance-related interference whatsoever for use in the antiviral testing.

Microscopic Findings Concerning the Analysis of Cell Morphology

In parallel preparations for determining metabolic performance in the enzymatic MTT assay, the influence of the test substances on the cells was determined by means of the microscopic assessment of cell morphology on day 3 or day 5 after assay preparation via the following criteria:

no change in cell morphology (−),
cells with slight vacuole formation (+),
enlarged cells and severe vacuole formation (++),
rounded cells (+++),
a destroyed cell lawn (++++),
a fixed cell lawn owing to possible surface-active ingredients (F) and
owing to precipitation of medium components on the cell lawn (N).

Testing of an Antiviral Effect

Antiviral activity was quantitatively analysed in plaque reduction assays and in virus-specific enzyme immunoassays.

Assays Used

Plaque Reduction Assay (PFU/ml)

Principle

To carry out the plaque reduction assays, confluently growing cells (cell lawn) were infected with a defined virus solution (M.O.I.=multiplicity of infection). After a one-hour incubation, the virus inoculum was removed and the cells (cell lawn) were washed. Afterwards, the virus-infected cells were overlaid with the physiological substance concentrations and the addition of a solid medium component (agarose or methylcellulose) and cultured further. The solid component in the overlaid medium limits the infection area, and so a focal point of virus-infected cells ("plaque") is formed. The various assay preparations were cultured until it was possible to observe microscopically the set plaque number (M.O.I.) in the untreated virus controls.

Evaluation

By fixing and staining the cell lawn, it was possible to render visible the virus plaques as bright rings in the dark-coloured cell lawn. Plaque number was determined using an image processing system.

Calculation of Percentage Inhibition (% Inhibition, Excel 2000 Statistics)

The plaque number of the untreated control was defined as 100% infection. In contrast, the plaque numbers of the various assay preparations were evaluated so that inhibitory effects of the substances to be analysed could be shown as percentage substance inhibition (% inhibition).

Enzyme Immunoassay (ELISA) (Analysis of Virus Production)

Principle

In the sandwich ELISA technique used here, the micro test strips are coated with antibodies against the specific viruses. The viruses situated in the cell culture supernatant of the infected cell lines bind to the solid phase-fixed antibodies. To render the reaction visible, use is made of labelled pathogen-specific detection antibodies with the enzyme peroxidase, which antibodies are directed against the corresponding viruses. In a further step, the substrate/chromogen and hydrogen peroxide and tetramethylbenzidine are added, leading to an enzyme-substrate-chromogen reaction to form a blue dye. The intensity of the colour is determined photometrically (absorbance) in a photometer at a wavelength of 450 nm (OD450); it is proportional to the content of virus antigen.

Procedure

Virus production in infected and treated cells was analysed by means of determining viral proteins (conserved virus-specific antigens in the case of RSV) in the ELISA. To this end, the confluently growing virus-sensitive cells (cell lawn) were infected with a defined virus solution (M.O.I.). After a one-hour incubation, the virus inoculum was removed and the infected cell lawn was washed. This was followed by the addition of the physiological substance concentrations. The various assay preparations were cultured until it was possible to observe microscopically a 70% to 90% CPE in the untreated virus controls. The newly synthesized viruses were situated in this stage in the cell culture supernatant. This was followed by the removal of the virus-containing cell culture supernatants for the analysis of the viral proteins in the ELISA.

Calculation of Percentage Inhibition (% Inhibition, Excel 2000 Statistics)

The absorbance values (OD492 nm) of the untreated controls, as determined in a photometer after the enzyme reactions in the ELISA, were defined as 100% infection. In contrast, the OD of the various assay preparations was evaluated so that inhibitory effects of the substances to be analysed could be shown as percentage substance inhibition (% inhibition).

Test Protocol

The virus-infected cells were treated with the test substances directly after infection. For this purpose, the virus-sensitive cells were infected with the various prepared virus solutions (HEp-2: RSV, HSV1; BGM: CA9; HeLa: HRV14). For the antiviral testing, the various virus infections were done with an intermediate infection dose (M.O.I. multiplicity of infection) of 0.0004 (RSV, HSV1, HRV14) or 0.0003 (CA9).

The addition of the test solutions in various dilution levels to the infected cells was carried out after checking for possible intoxication in the cell viability assays. The dilution series started with non-cell-toxic concentrations of 50 µg/ml (test samples No. 1 and No. 2), 2 µg/ml (test sample No. 3) and 6 µg/ml (test sample No. 4). The dilution was carried out in log 2 or log 10 graduations. Table 1 shows the test sample concentrations used in the antiviral testing.

The quantitative analysis of an antiviral activity was achieved in the plaque reduction assay by counting the virus plaques on day 3 to day 5 after assay preparation with the aid of an image processing system. In addition, in the case of RSV, in addition to the experiments relating to the virus plaque analysis, the cell culture supernatants of the infected and treated cells were tested for the content of newly synthesized viral proteins in enzyme immunoassays (ELISA) in similarly implemented assay preparations.

The test system was verified by using active antiviral substances: ribavirin (Virazole®) against RSV, aciclovir (Zovirax®) against HSV1 and oxymetazoline hydrochloride (OMZ) against HRV14. A concentration of 10 µg OMZ/ml, 5 µg of ribavirin per ml or 2.5 µg of aciclovir per ml at the M.O.I. of 0.0004 used yielded on average a reduction in infectivity of about 50-60%. In the case of CA9, laboratory internal standards were included. The laboratory internal standards were set such that it was possible to demonstrate a 50% to 70% reduction in infectivity.

Furthermore, in the test system, the ethanolic solvent of the various test solutions in the final concentrations of 0.8% (No. 1, No. 2), 0.0043% (No. 3) and 0.048% (No. 4) EtOH in the medium (MEM) was included in addition to the positive controls. This made it possible to establish that there was no influence on the development of the virus plaques or on the infectivity of the viruses.

TABLE 1

Test sample concentrations used in the antiviral testing

| Test sample | Concentrations [µg/ml] for the antiviral testing | | | | | | | | |
|---|---|---|---|---|---|---|---|---|---|
| No. 1 AT | 100 | 50 | 25 | 12.5 | 6.25 | 3.125 | 1.56 | 0.78 | 0.156 | 0.078 |
| No. 2 AC | 100 | 50 | 25 | 12.5 | 6.25 | 3.125 | 1.56 | 0.78 | 0.156 | 0.078 |
| No. 3 QC | 2 | 1 | 0.5 | 0.25 | 0.125 | 0.08 | 0.06 | 0.04 | 0.02 | 0.01 |
| No. 4 AT/AC/QC | 6.004 | 3.002 | 2.000 | 1.500 | 1.000 | 0.750 | 0.500 | 0.380 | 0.250 | 0.19 |

TABLE 1-continued

Test sample concentrations used in the antiviral testing

| Test sample | Concentrations [µg/ml] for the antiviral testing | | | | | | |
|---|---|---|---|---|---|---|---|
| No. 1 AT | 0.0078 | | | | | | |
| No. 2 AC | 0.0078 | | | | | | |
| No. 3 QC | 0.006 | 0.005 | 0.0025 | 0.0012 | 0.0006 | 0.00006 | 0.000006 |
| No. 4 AT/ AC/ QC | 0.025 | 0.02 | | | | | |

Synergistic Effect of Mixture of Atropine Sulphate, Aconitine and Mercury Cyanide

TABLE 2

Comparison of the antiviral effect between the substances atropine sulphate, aconitine and mercury cyanide and also the mixture thereof. Here, the percentage plaque inhibition is reported as the measurement results. The measurement results of the individual substances are reported for the concentration range corresponding to that present in the mixture.

| Virus | Atropine sulphate (3.125-6.25 µg/ml) | Aconitine (0.156-1.56 µg/ml) | Mercury cyanide (0.0025-0.006 µg/ml) | Mixture (6.004 µg/ml) |
|---|---|---|---|---|
| HSV1 | 19.52/41.90 | 3.17/11.22 | 0.00/−1.39 | 69.53 |
| CA9 | 7.63/12.85 | 8.40/10.69 | −2.32/0.00 | 39.16 |

TABLE 2-continued

Comparison of the antiviral effect between the substances atropine sulphate, aconitine and mercury cyanide and also the mixture thereof. Here, the percentage plaque inhibition is reported as the measurement results. The measurement results of the individual substances are reported for the concentration range corresponding to that present in the mixture.

| Virus | Atropine sulphate (3.125-6.25 µg/ml) | Aconitine (0.156-1.56 µg/ml) | Mercury cyanide (0.0025-0.006 µg/ml) | Mixture (6.004 µg/ml) |
|---|---|---|---|---|
| RSV | 7.74/12.36 | 9.01/16.56 | −3.20/5.33 | 42.41 |
| HRV14 | 11.30/14.12 | −1.14/2.84 | 15.48*) | 34.04 |

*)Only one value was measured.

In Table 2 are the values for the antiviral effect, measured on the basis of the percentage inhibition of viral activity, of atropine sulphate, aconitine and mercury cyanide and also of the mixture of these three substances. In the case of the individual substances, only those measurement values which were measured in the concentration ranges corresponding to those of the individual substances in the mixture are reported. The following substance concentrations were present in the mixture: 5 µg/ml atropine sulphate, 1 µg/ml aconitine and 0.004 µg/ml mercury cyanide.

Table 2 clearly shows that, firstly, the overall effect of the mixture is greater than the effect of the substances on their own and, secondly, the antiviral effect of the mixture is not based on an addition of the antiviral effect of the individual substances, but on a synergistic effect. For example, if there is an additive effect in the case of the antiviral effect on HSV1, the measurement values of the mixture would have to be between 22.69 and 51.73, but this is not the case. In fact, the mixture exhibits a value of 69.53.

TABLE 3

In vitro assay of the antiviral effect of pharmaceutical composition depending on the concentration, measured as percentage relative inhibition (see FIG. 1)

| Viruses | Concentrations [µg/ml] | | | | | | | | | | | |
|---|---|---|---|---|---|---|---|---|---|---|---|---|
|  | 6 | 3 | 2 | 1.5 | 1 | 0.75 | 0.5 | 0.375 | 0.25 | 0.19 | 0.025 | 0.019 |
| HRV14 | 34.04 | 18.62 | 0.53 | — | −2.13 | — | 2.66 | — | −3.72 | — | −1.06 | — |
| RSV | 42.41 | 26.18 | — | 7.85 | — | 2.36 | — | −1.57 | — | −2.36 | — | 0.52 |
| CA9 | 39.16 | 24.92 | — | 5.18 | — | −1.94 | — | −2.27 | — | −0.32 | — | −3.24 |
| HSV1 | 69.53 | 44.23 | — | 13.76 | — | 1.47 | — | 2.70 | — | −3.44 | — | 0.00 |

The invention claimed is:

1. A method of treating a patient who has a viral infection caused by a herpesvirus, an adenovirus, and/or an enterovirus, the method comprising administering to the patient an effective amount of a pharmaceutical composition comprising
   (a) atropine sulphate;
   (b) aconitine; and
   (c) mercury cyanide;
   wherein the composition is administered to the patient in a daily total dose of 20 µg±30% atropine sulphate, 4 µg±30% aconitine and 0.016 µg±30% mercury cyanide.

2. The method of claim 1, wherein the viral infection is caused by HSV1 (herpes simplex virus type 1), and/or CA9 (human coxsackievirus type 9).

3. The method of claim 1, wherein the composition is an aqueous/ethanolic solution and comprises about 5 µg/ml atropine sulphate, about 1 µg/ml aconitine and about 0.004 µg/ml mercury cyanide.

4. The method of claim 1, wherein the composition contains between 1-10 μg/ml atropine sulphate.

5. The method of claim 1, wherein the composition contains between 0.05-5 μg/ml aconitine.

6. The method of claim 1, wherein the composition contains between 0.001 and 0.1 μg/ml mercury cyanide.

7. The method of claim 4, wherein the composition contains about 2-7 μg/ml atropine sulfate.

8. The method of claim 4, wherein the composition contains about 3.13-6.25 μg/ml atropine sulfate.

9. The method of claim 5, wherein the composition contains about 0.5-2 μg/ml aconitine.

10. The method of claim 5, wherein the composition contains about 0.16-1.56 μg/ml aconitine.

11. The method of claim 6, wherein the composition contains about 0.001-0.01 μg/ml mercury cyanide.

12. The method of claim 6, wherein the composition contains about 0.003-0.006 μg/ml mercury cyanide.

\* \* \* \* \*